United States Patent
Norton et al.

(10) Patent No.: US 8,280,519 B2
(45) Date of Patent: Oct. 2, 2012

(54) METHOD OF MAINTAINING WET-TANTALUM ELECTROLYTIC CAPACITORS

(75) Inventors: John D. Norton, New Brighton, MN (US); Ann M. Crespi, Mobile, AL (US); Darrel F. Untereker, Oak Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 13/343,092

(22) Filed: Jan. 4, 2012

(65) Prior Publication Data

US 2012/0105017 A1    May 3, 2012

Related U.S. Application Data

(62) Division of application No. 11/323,027, filed on Dec. 30, 2005, now Pat. No. 8,112,158.

(51) Int. Cl.
*A61N 1/00* (2006.01)
*H01G 9/04* (2006.01)

(52) U.S. Cl. ............... 607/59; 607/5; 361/508
(58) Field of Classification Search ........... 607/5, 59; 361/508
See application file for complete search history.

(56) References Cited

U.S. PATENT DOCUMENTS

| | | | |
|---|---|---|---|
| 5,737,181 A | 4/1998 | Evans |
| 5,741,307 A | 4/1998 | Kroll |
| 5,792,188 A | 8/1998 | Starkweather et al. |
| 5,861,006 A | 1/1999 | Kroll |
| 5,982,609 A | 11/1999 | Evans |
| 6,096,602 A | 8/2000 | Kim et al. |
| 6,212,063 B1 | 4/2001 | Johnson et al. |
| 6,283,985 B1 | 9/2001 | Harguth et al. |
| 6,409,776 B1 | 6/2002 | Yan et al. |
| 6,452,777 B1 | 9/2002 | Naito |
| 6,706,059 B2 | 3/2004 | Harguth et al. |
| 7,038,901 B2 | 5/2006 | Muffoletto et al. |
| 7,131,988 B2 | 11/2006 | Harguth et al. |
| 7,203,539 B2 | 4/2007 | Ware et al. |
| 7,256,982 B2 | 8/2007 | Lessner et al. |
| 2001/0047190 A1 | 11/2001 | Harguth et al. |
| 2003/0088273 A1 | 5/2003 | Liu et al. |
| 2004/0064157 A1 | 4/2004 | Norton |
| 2004/0186519 A1 | 9/2004 | Norton |
| 2004/0186520 A1 | 9/2004 | Harguth et al. |
| 2004/0225327 A1 | 11/2004 | Norton et al. |
| 2004/0243183 A1 | 12/2004 | Norton et al. |
| 2005/0027318 A1 | 2/2005 | Ware et al. |
| 2005/0180094 A1 | 8/2005 | Muffoletto et al. |

FOREIGN PATENT DOCUMENTS

| | | |
|---|---|---|
| JP | 05121275 A | 5/1993 |
| WO | 03045497 A2 | 6/2003 |

*Primary Examiner* — Nicole F Lavert

(57) ABSTRACT

Wet-tantalum capacitors used in a medical device are charged to and maintained at a maintenance voltage between full energy charges so that deformation in the wet-tantalum capacitor is substantially inhibited.

7 Claims, 2 Drawing Sheets

METHOD OF MAINTAINING WET-TANTALUM ELECTROLYTIC CAPACITORS

RELATED APPLICATIONS

This application is a divisional of U.S. application Ser. No. 11/323,027, filed Dec. 30, 2005, now U.S. Pat. No. 8,112,158, the disclosure of which is incorporated by reference in its entirety herein.

BACKGROUND OF THE INVENTION

The present invention relates generally to electrolytic capacitors. In particular, the present invention relates to maintaining wet-tantalum capacitors used in medical devices to deliver high energy electrical therapy to a patient.

Implantable cardioverter defibrillators (ICD's) and automatic external defibrillators (AED's) apply a therapeutic electric shock to a patient's heart to restore the heart to a normal rhythm. These devices use high voltage capacitors that are charged just before the cardioversion or defibrillation therapy is delivered, and then discharged through electrodes to deliver the therapeutic electrical shock. Wet electrolytic capacitors are typically used in ICD's and AED's. A wet electrolytic capacitor includes a metallic anode, a metal oxide layer formed on the anode, a liquid electrolyte, and a cathode.

Originally, aluminum electrolytic capacitors having an aluminum anode with an aluminum oxide coating were used. More recently, wet-tantalum capacitors having a tantalum anode, a tantalum oxide dielectric layer, a liquid electrolyte, and a cathode (e.g., a tantalum or ruthenium oxide) have been developed for use in ICDs and AEDs.

When wet electrolytic capacitors rest on open circuit for days or longer, a process commonly referred to as "deformation" occurs. As a result, when the capacitor is next charged, an appreciable amount of energy is used to "reform" the oxide dielectric layer. This results in longer than desired charging times for the ICD or AED. It also affects the longevity of the device, because a greater amount of energy from the battery is required during the charging process.

Techniques for reforming electrolytic capacitors in ICD's are discussed in Kroll U.S. Pat. No. 5,741,307; Startweather et al. U.S. Pat. No. 5,792,188; Kroll U.S. Pat. No. 5,861,006; and Silvian U.S. Pat. No. 6,096,602. These patents describe reform techniques which were originally used with aluminum electrolytic capacitors.

Wet-tantalum capacitors exhibit less severe deformation than aluminum electrolytic capacitors, but degradation of wet-tantalum capacitors and techniques for reforming the tantalum/tantalum oxide anode have also been addressed. Methods of reforming wet-tantalum capacitors are described in Harguth et al. U.S. Pat. Nos. 6,283,985 and 6,706,059, Liu et al. Publication No. U.S. 2003/0088273; and Norton et al. U.S. Pat. No. 7,917,217.

BRIEF SUMMARY OF THE INVENTION

The present invention maintains a wet-tantalum capacitor used in a medical device so that deformation is substantially inhibited. Tantalum electrolytic capacitor deformation is controlled by maintaining the capacitor at a maintenance voltage between full energy charges. The maintenance voltage inhibits processes which cause deformation to occur, without causing significant power loss due to capacitor leakage.

DETAILED DESCRIPTION

The deformation of wet-tantalum capacitors is attributed to two related causes. The first contributor is incomplete or poor formation of the anodic oxide (i.e. the $Ta_2O_5$ dielectric layer) associated with the deposition of a sparingly soluble phosphate species in the interstices of the anode during formation of the anodic oxide. The second contributor is the operation of the capacitor at voltages above the onset of significant parasitic reactions (those not associated with oxide formation or capacitive charging), which result in similar deposits of phosphates within the anode.

It is believed the deformation mechanism is the result of hydration of either the $Ta_2O_5$ dielectric or, more likely, of the phosphate deposit within the interstices of the anode. When the capacitor is "fully formed", the phosphate deposit exists in a dehydrated state. As the capacitor rests at open circuit with no voltage applied, hydration of the phosphate makes it more conductive, allowing electrical access to more $Ta_2O_5$ surface area. This increases the amount of energy that is required to charge the capacitor relative to that required for a fully formed capacitor. Because of the relatively high resistance of the hydrated phosphate, the additional capacitance is realized only during the relatively slow capacitor charging process, and not during the much more rapid discharge.

Reformation of the capacitor requires dehydration of the phosphate deposit. The dehydration process is assisted by the application of an electric field. It has been discovered that the electric field required is relatively low compared to that applied when the capacitor is charged to a high voltage relative to its voltage or maximum energy voltage. As such, capacitor reformation has been achieved at relatively low voltages, as described in U.S. Pat. No. 7,917,217.

The present invention addresses the issue of deformation by preventing the deformation process from taking place, rather than by performing periodic reformation charging and discharging of the capacitor. The process of deformation may be prevented by maintaining the capacitor at a maintenance voltage between full energy charges. Because the power lost to capacitor leakage current can be very low at these voltages, it does not significantly impact battery life, and therefore ICD device longevity is not impacted.

The maintenance voltage can range from a voltage that at least partially inhibits deformation up to a voltage of about 90% of rated voltage. Generally, the lower the maintenance voltage, the lower the capacitor leakage current. Therefore, maintenance voltages less than about 50%, and particularly about 25% or less of rated voltage will result in lower losses of charge through capacitor leakage current. Selection of a maintenance voltage may involve striking a balance between the amount of energy consumed by leakage and the extent of deformation (if any) that is acceptable.

Figure 1:
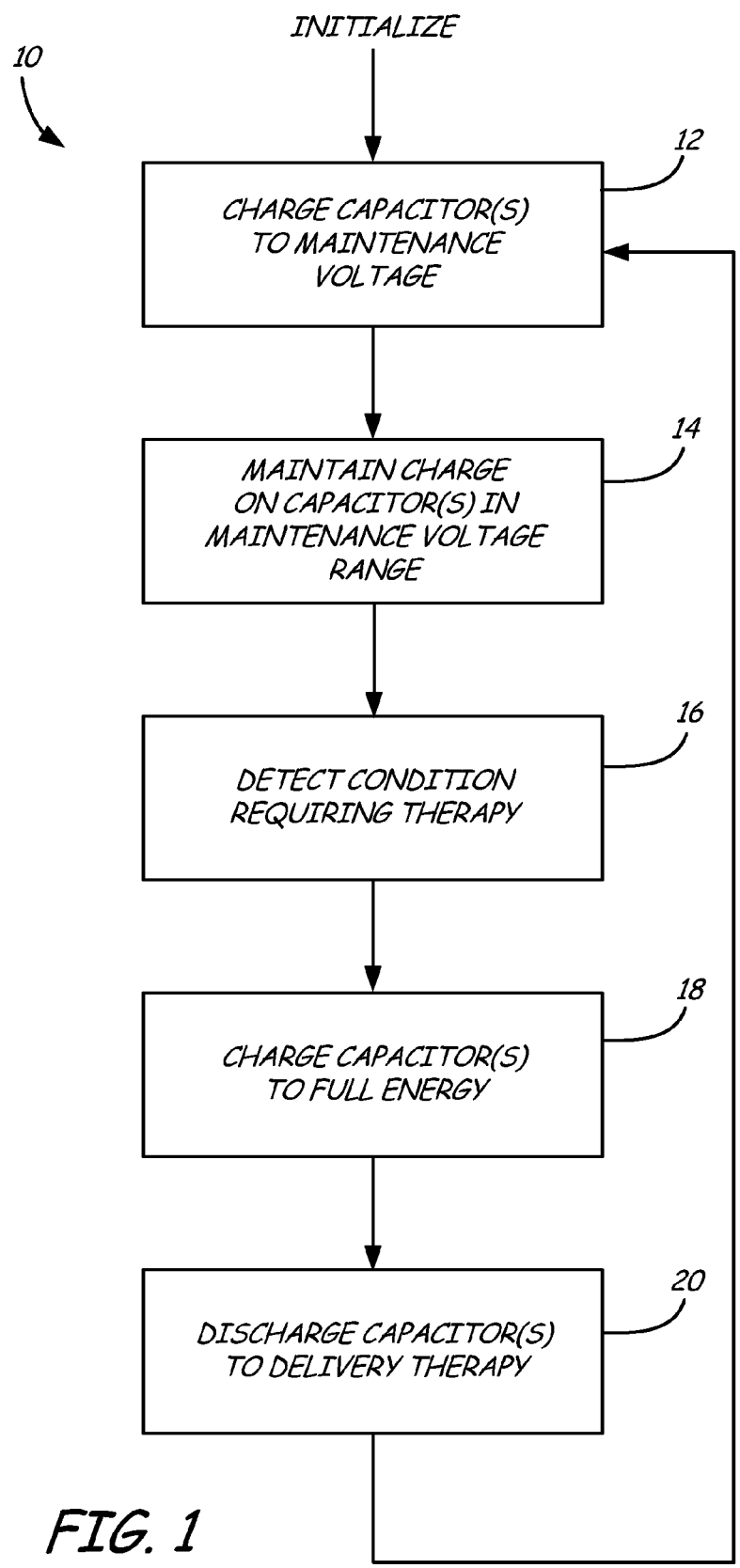
FIG. 1 is a flow diagram illustrating a method of maintaining a wet-tantalum capacitor to inhibit deformation.

FIG. 1 illustrates method 10 of operating a medical device in a way that inhibits deformation effects in its high voltage wet-tantalum capacitors. When the medical device is initialized, the wet-tantalum capacitors are charged to a maintenance voltage, which is a voltage at which phosphate deposits the anode to the capacitor will be maintained in a substantially dehydrated state (step 12). This voltage, therefore, will substantially inhibit deformation from taking place.

The charge on the capacitors is maintained within a maintenance voltage range (step 14) until there is a need to deliver therapy. The voltage on the capacitors may be sensed, and an additional charge may be delivered to the capacitors from time-to-time in order to maintain the voltage on the capacitors within the desired maintenance voltage range.

At step 16, the medical device has detected a condition requiring therapy. For example, a malignant tachycardia may have been detected, based upon electrogram (EGM) or electrocardiogram (ECG) signals sensed by the device.

At step 18, upon determining that therapy will be required, the device causes the wet-tantalum capacitors to be charged to full energy (i.e. the energy level programmed in the device for the cardioversion or defibrillation shock). Because the capacitors are already partially charged to the maintenance voltage range, and deformation has been substantially inhibited, the charging time to reach full energy is reduced compared to a similar capacitor beginning at an uncharged state.

When the device senses that the capacitors are charged to the desired (full energy) voltage level, the device makes a final determination of whether to deliver the therapy. If a condition requiring therapy is still present, the capacitors are discharged to deliver therapy to the patient (step 20).

Once the capacitors have been discharged, they will again be charged to at least the maintenance voltage (step 12) and maintained at that voltage (step 14) until therapy is again needed. This may be a very short time period, depending upon whether an additional defibrillation shock is needed. Alternatively, if multiple shocks are required, charging again to full energy may occur without any significant period at which the capacitor remains at the maintenance voltage level. In some cases, the full energy level may be increased with successive shocks.

Figure 2:
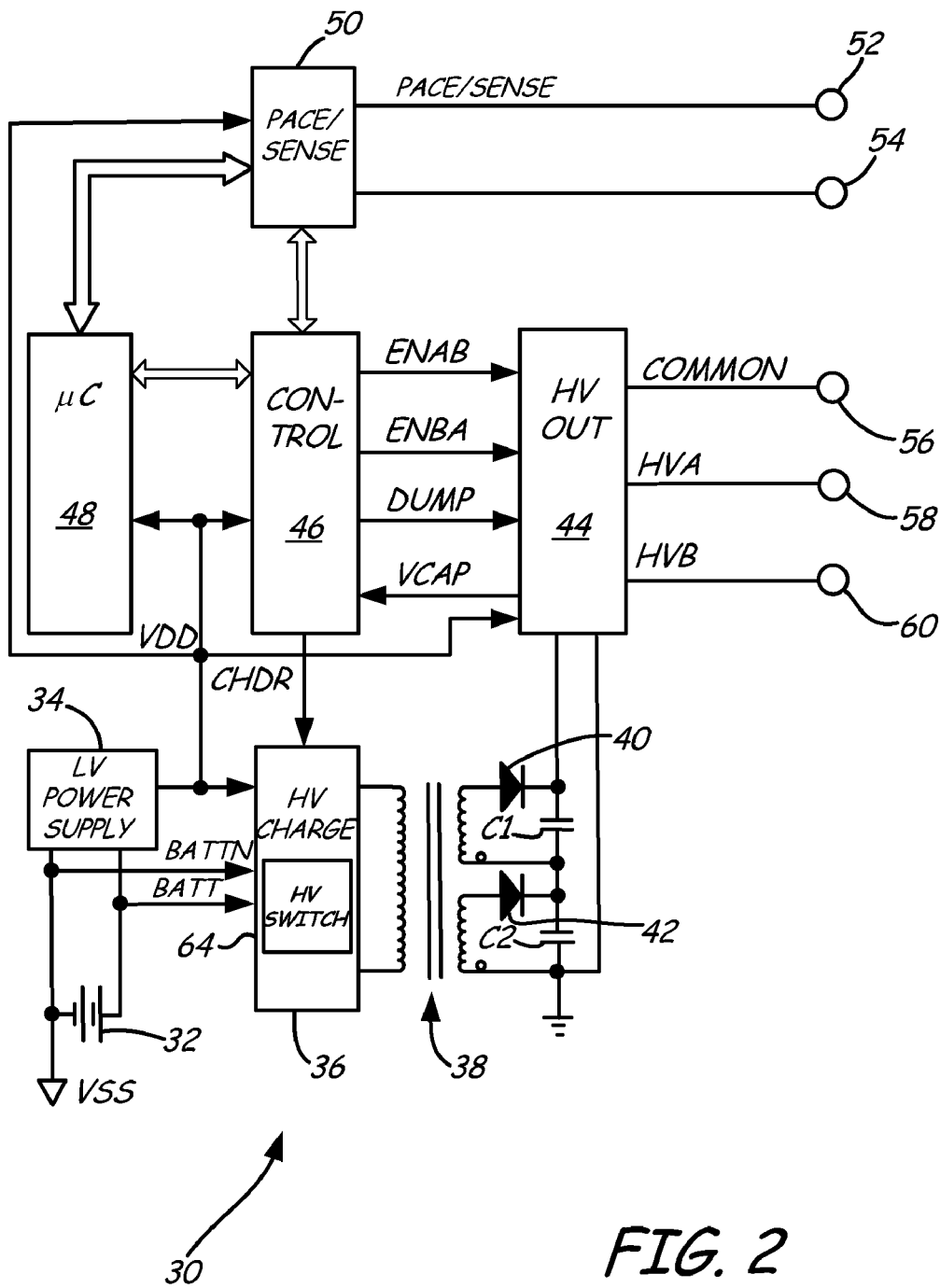
FIG. 2 is a block diagram of an example of an ICD in which the maintenance method of FIG. 1 can be used.

FIG. 2 shows ICD 30, which is an example of a medical device in which the capacitor maintenance of the present invention can be implemented. ICD 30 includes battery 32, low voltage power supply 34, high voltage charging circuit 36, transformer 38, diodes 40 and 42, wet-tantalum capacitors C1 and C2, high voltage output circuit 44, control 46, microcomputer 48, pace/sense circuitry 50, pace/sense terminals 52 and 54, and cardioversion/defibrillation terminals 56, 58, and 60.

Battery 32 provides power through low voltage power supply 34 with the electrical circuitry of ICD 30. In addition, battery 32 supplies power to high voltage charging circuit 36 that is used to charge capacitors C1 and C2. High voltage charging circuit 36 and transformer 38 step up the relatively low voltage of battery 32 to the voltage levels needed to charge capacitors C1 and C2 to full energy, as well as to the maintenance voltage.

Pace/sense terminals 52 and 54 are connected to pace/sense electrodes (not shown) used to sense electrical activity of the heart, and to deliver pacing pulses under the control of pace/sense circuitry 50. The pace/sense electrodes are carried by leads connected to terminals 52 and 54, or may be carried on the housing or can of ICD 30.

Pace/sense circuitry 50 receives EGM signals from terminals 52 and 54 and senses R-wave activity. In conjunction with microcomputer 48 and control 46, pace/sense circuitry 50 delivers pacing pulses to terminals 52 and 54.

The sensed R-wave activity is also used by microcomputer 48 and control 46 to determine presence of a malignant tachycardia that requires cardioversion/defibrillation shocks. Upon determining the need for cardioversion/defibrillation, control 46 causes high voltage charging circuit 36 to charge capacitors C1 and C2 to full energy. High voltage output circuit 44 senses the voltage on capacitors C1 and C2, and provides a feedback signal VCAP to control 46. When control 46 detects that VCAP signal matches the programmed energy levels for the cardioversion/defibrillation shock, control 46 provides control signals (ENAB and ENBA) to the output circuit 44.

Capacitors C1 and C2 are discharged between defibrillation electrodes connected to terminals 58 and 60 and a common or can electrode on the housing of ICD 30 (which is connected to terminal 56). The high voltage therapeutic discharges may be delivered simultaneously or sequentially, or discharge may be provided between only one of the terminals 58 and 60 and common terminal 56. If the therapeutic discharge is terminated at a voltage that is greater than the maintenance voltage, capacitors C1 and C2 may be discharged or allowed to bleed down to the maintenance voltage prior to initiation of any maintenance charging.

Charging of capacitors C1 and C2 may begin before a final decision is made to deliver cardioversion/defibrillation therapy. If normal rhythm returns and a therapeutic shock is not required, control 46 provides a DUMP control signal to high voltage output circuit 44, which causes the energy on capacitors C1 and C2 to be discharged through a non-therapeutic load within ICD 30, until they reach the maintenance voltage (or alternatively are fully discharged).

During time periods between full energy charging and discharging of capacitors C1 and C2, control 46 causes capacitors C1 and C2 to be charged to the maintenance voltage. Control 46 monitors the voltage on C1 and C2 with the VCAP feedback signal. If the voltage on C1 and C2 decreases to a point at which deformation can occur, control 46 causes high voltage charging circuit 36 to increase charge on C1 and C2 so that they are maintained in a voltage range at which deformation is inhibited.

This maintenance method addresses deformation by creating conditions that reduce the extent to which deformation of the capacitor anode can occur. As a result, periodic reformation charging and discharging is unnecessary.

The maintenance method results in decreased device charging times because the effects of deformation are reduced or eliminated. In addition, the capacitors are maintained in a partially charged condition, which also decreases charging time when therapy is needed.

The maintenance method also increases device longevity. Less energy is used to charge and maintain the capacitor to a low level than is used in periodically reforming the capacitor by charging and then discharging it. Although the method has been described in a specific implementation of an ICD shown in FIG. 2, the invention can be implemented with other ICD's with different numbers of capacitors, different numbers of electrodes, and different circuitry than that shown in FIG. 2. Similarly, the method is applicable to other medical devices (including AEDs) where charging and discharging of wet-tantalum electrolytic capacitors, with intervening periods of inactivity, occur. Although particularly beneficial for implantable medical devices, where capacitor size and battery life are important, deformation of wet-tantalum capacitors can cause delays in charging other devices as well, including external medical devices as well as devices and systems having non-medical uses.

Although the present invention has been described with reference to preferred embodiments, workers skilled in the art will recognize that changes may be made in form and detail without departing from the spirit and scope of the invention.

The invention claimed is:

1. A method of maintaining a wet-tantalum capacitor in a medical device that is charged to full energy and discharged to provide a therapy to a patient, the method comprising:
   charging the capacitor to a maintenance voltage range at which deformation effects are reduced; and
   once the capacitor is charged to the maintenance voltage range, always maintaining charge on the capacitor within the maintenance voltage range until the capacitor is again charged to full energy.

2. The method of claim 1, wherein the maintenance voltage range include voltages at which deformation is at least partially inhibited.

3. The method of claim 2, wherein the maintenance voltage range includes voltages of up to about 90% of a rated voltage of the capacitor.

4. The method of claim 2, wherein the maintenance voltage range includes voltages of up to about 50% of the rated voltage.

5. The method of claim 2, wherein the maintenance voltage range includes voltages of up to about 25% of the rated voltage.

6. A method of maintaining a wet-tantalum capacitor, comprising:
   charging the capacitor to a maintenance voltage range that is less than one of a maximum and rated voltage for the capacitor; and
   once the capacitor is charged to the maintenance voltage range, always maintaining charge on the capacitor within the maintenance voltage range between full energy charging events.

7. The method of claim 6, wherein the maintenance voltage range include voltages at which deformation is at least partially inhibited.

* * * * *